United States Patent
Fabien (10) Patent No.: US 12,171,987 B2
(45) Date of Patent: Dec. 24, 2024

(54) AUTOINJECTOR

(71) Applicant: APTAR FRANCE SAS, Le Neubourg (FR)

(72) Inventor: David Fabien, Corseul (FR)

(73) Assignee: APTAR FRANCE SAS, Le Neubourg (FR)

( * ) Notice: Subject to any disclaimer, the term of this patent is extended or adjusted under 35 U.S.C. 154(b) by 943 days.

(21) Appl. No.: 17/277,581

(22) PCT Filed: Sep. 19, 2019

(86) PCT No.: PCT/FR2019/052192
§ 371 (c)(1),
(2) Date: Mar. 18, 2021

(87) PCT Pub. No.: WO2020/058639
PCT Pub. Date: Mar. 26, 2020

(65) Prior Publication Data
US 2022/0023541 A1    Jan. 27, 2022

(30) Foreign Application Priority Data
Sep. 20, 2018 (FR) ........................... 1858533

(51) Int. Cl.
*A61M 5/20* (2006.01)
*A61M 5/24* (2006.01)
(Continued)

(52) U.S. Cl.
CPC ........ *A61M 5/2033* (2013.01); *A61M 5/2422* (2013.01); *A61M 5/31515* (2013.01);
(Continued)

(58) Field of Classification Search
CPC .............. A61M 5/2033; A61M 5/2422; A61M 2005/244; A61M 5/326;
(Continued)

(56) References Cited

U.S. PATENT DOCUMENTS 5,865,804 A    2/1999  Bachynsky
6,149,626 A    11/2000 Bachynsky et al.
(Continued)

FOREIGN PATENT DOCUMENTS

| EP | 2 438 946 A1 | 4/2012 |
| EP | 2 705 862 A1 | 3/2014 |
| WO | 2019/016345 A1 | 1/2019 |

OTHER PUBLICATIONS

International Preliminary Report on Patentability issued Nov. 9, 2020 in International Application No. PCT/FR2019/052192.

*Primary Examiner* — Nilay J Shah
(74) *Attorney, Agent, or Firm* — Sughrue Mion, PLLC (57) ABSTRACT

An autoinjector having a reservoir (100) containing fluid and a piston; a needle; a driver (200) having a body; a piston rod (210) movable between a rest position and an injection position; an injection spring (220); and a force control mechanism (280, 290) for causing the force exerted by the injection spring to vary in predetermined manner during injection, and a lever (280) and a cam (290), the lever (280) pivotally mounted on the piston rod, being connected to the injection spring (220), and co-operating with the cam; and an interface module (300) fastened to the driver that receives a reservoir (100) before each actuation. The interface module having a selector ring (310) mounted to turn on the driver module, and pivot elements (320) fastening the reservoir module in the interface module.

12 Claims, 7 Drawing Sheets

(51) Int. Cl.
*A61M 5/315* (2006.01)
*A61M 5/32* (2006.01)
*A61M 5/145* (2006.01)

(52) U.S. Cl.
CPC ......... *A61M 5/326* (2013.01); *A61M 5/14566* (2013.01); *A61M 2005/206* (2013.01); *A61M 2005/2073* (2013.01); *A61M 2005/2086* (2013.01); *A61M 2005/2407* (2013.01); *A61M 5/31543* (2013.01); *A61M 5/31591* (2013.01)

(58) Field of Classification Search
CPC .. A61M 2005/2407; A61M 2005/2433; A61M 2005/206; A61M 2005/2073; A61M 5/31591; A61M 5/14566
See application file for complete search history.

(56) References Cited

U.S. PATENT DOCUMENTS

| | | | | |
|---|---|---|---|---|
| 6,599,272 B1 * | 7/2003 | Hjertman | ............... | A61M 5/315 604/209 |
| 2003/0105430 A1 * | 6/2003 | Lavi | ................... | A61M 5/2033 604/890.1 |

* cited by examiner

AUTOINJECTOR

CROSS REFERENCE TO RELATED APPLICATIONS

This application is a National Stage of International Application No. PCT/FR2019/052192 filed Sep. 19, 2019, claiming priority based on French Patent Application No. 1858533 filed Sep. 20, 2018.

The present invention relates to an autoinjector.

Autoinjectors are well known in the prior art. The purpose of such devices is mainly to inject the contents of a syringe or of a cartridge automatically into a patient's body. Various systems exist for making the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, the cost of manufacture and of assembly is also a factor that needs to be taken into account.

Numerous autoinjectors exist on the market that may present drawbacks.

Thus, autoinjectors generally use one or more springs, held cocked before triggering, so as to perform injection proper, and sometimes also jabbing. The springs may be of any type, in particular traction, compression, torsion, spiral, or others. In most circumstances, the force generated by the spring and available for thrusting the piston during expulsion of the fluid is associated directly with the force/length characteristics or other dimensional parameters of the spring, such as angle for a torsion spring. The injection spring then exerts a maximum force at the beginning, with this force progressively decreasing during the injection stage. This may in particular present problems depending on the viscosity of the fluid to be dispensed. Furthermore, the spring should present thrust that is large at the beginning of injection, so as to guarantee that the injection stage is performed in full, which can make the beginning of the injection stage painful.

Ideally, it should in fact be possible to modulate the force applied by the spring(s) of the autoinjector on the piston rod during the actuation stroke in order to adapt to the various steps encountered by the piston during expulsion. Thus, while docking the piston rod on the piston, it is necessary to avoid an impact that is too violent, in order to avoid damaging or breaking the reservoir, in particular the collar for a syringe. In contrast, storage can lead to a phenomenon of the piston jamming in the reservoir, and this requires a spike of force to initiate movement of the piston. In addition, as a result of their characteristics, certain fluids may require force to vary during expulsion. Mention may thus be made of non-Newtonian fluids that have the distinctive feature of having viscosity that depends on the speed of the molecules. Thus, during the first millimeters of the stroke of the piston, a spike of force is necessary in order to initiate the movement of the piston. Furthermore, certain very viscous fluids require a large force to be applied on the piston, typically lying in the range about 100 newtons (N) to about 200 N. However, the force required to trigger this very large expulsion force must remain acceptable for the user, and typically lie in the range about 4 N to about 8 N On another topic, a critical point of present-day autoinjectors, which are generally single-use autoinjectors, is that their main function, namely to dispense fluid, cannot be tested beforehand, prior to use by the final user.

Another problem arises with certain autoinjectors, in particular with autoinjectors that are for single-use and are thus disposed of after use. Unfortunately, such a complex device comprises numerous parts, and in particular metal parts, such as springs, and this poses recycling problems. Specifically, it is potentially difficult to recycle the metal of an autoinjector since it is subject to clinical waste regulations (DASRI in French legislation).

Documents EP 2 438 946, U.S. Pat. No. 6,149,626, EP 2 705 862, US 2003/105430, and U.S. Pat. No. 5,865,804 describe prior-art devices.

An object of the present invention is to provide an autoinjector that does not have the above-mentioned drawbacks.

Another object of the present invention is to provide an autoinjector with a predetermined force profile throughout the injection stage.

Another object of the present invention is to provide an autoinjector having a major portion that is reusable, with a portion that is disposable after each actuation that does not contain metal.

Another object of the present invention is to provide an autoinjector that the manufacturer can test before putting into the hands of the user.

Another object of the present invention is to provide an autoinjector that is reliable and safe in use, that makes it possible to guarantee that all of the fluid is dispensed to the desired location, and that is simple and inexpensive to manufacture and to assemble.

The present invention thus provides an autoinjector comprising:
- a reservoir module comprising a reservoir containing fluid and a piston, and including a needle;
- a driver module comprising:
  - a body;
  - a piston rod that co-operates with the piston of said reservoir, said piston rod being moved between a rest position and an injection position in which said piston rod has moved the piston of the reservoir so as to inject the fluid through said needle;
  - an injection spring for urging said piston rod towards its injection position; and
  - force control means, for causing the force exerted by said injection spring on said piston rod to vary in predetermined manner throughout the injection stage, said force control means comprising a lever and a cam, said lever being pivotally mounted at one end on said piston rod, being connected to said injection spring, and co-operating at its other end with said cam; and
- an interface module that is fastened to the driver module and that receives a reservoir module before each actuation, said interface module comprising a selector ring that is mounted to turn on the driver module, and pivot elements for fastening the reservoir module in the interface module.

Advantageously, said reservoir module further comprises an actuator sleeve that is movable relative to said reservoir between a deployed position in which it is arranged around said needle, and an actuated position in which it is moved axially relative to the reservoir so as to expose the needle.

Advantageously, said autoinjector further comprises an interface module that is fastened to the driver module and that receives a reservoir module before each actuation.

Advantageously, said interface module comprises a selector ring that is mounted to turn on the driver module, and pivot elements for fastening the reservoir module in the interface module.

Advantageously, said selector ring is movable in turning between a locked position in which insertion of a reservoir module is possible and actuation of the driver module is not possible, an injection position in which actuation of the driver module is possible, a safety position in which an actuator sleeve of the reservoir module returns into its deployed position around said needle, and an ejection position in which ejection of the used reservoir module is possible.

Advantageously, said driver module includes a lock that blocks said piston rod in its rest position, said lock comprising a thread that is connected at one end to said piston rod and at its other end to a toothed winder wheel, a locking member co-operating with a tooth of said toothed winder wheel, said locking member being movable, in particular pivotable, between a blocking position in which it prevents the winder wheel from turning in the direction of the actuation force exerted by said injection spring on said piston rod, and an actuated position in which said turning of the winder wheel is possible.

Advantageously, a deflector wheel forming a pulley for the thread is provided between said piston rod and said winder wheel.

Advantageously, said locking member includes an extension that is adapted to co-operate with an actuator sleeve of the reservoir module when said needle has jabbed the site that is to be injected, so as to move said locking member towards its actuated position.

Advantageously, said autoinjector includes re-cocking means, such as a knob, for rewinding said thread on said winder wheel by turning said winder wheel in the opposite direction to its direction during the injection stage.

Advantageously, said injection spring is fastened at one end to said body and at its other end to said lever, one end of said lever being pivotable about said piston rod and its other end being movable along said cam.

Advantageously, said lever performs both a pivoting movement about a point of said piston rod and also a movement in translation relative to said body, these two movements being linked and performed in a single plane.

These and other characteristics and advantages appear more clearly from the following detailed description, given by way of non-limiting example, and with reference to the accompanying drawings, in which.

The autoinjector is described below with reference to several advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shapes that are different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

In the embodiment shown in the drawings, the autoinjector comprises three distinct portions or modules: a reservoir module 100, a driver module 200, and an interface module 300.

Figure 1:
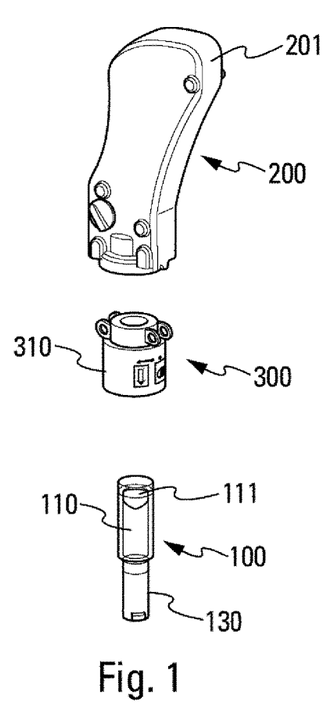
FIG. 1 is an exploded diagrammatic side view in perspective of the three modules of an autoinjector, in an advantageous embodiment.

FIG. 1 shows the three separate modules, and FIGS. 2 to 12 show the full reservoir module being put into place, the driver module being actuated, and the empty reservoir module being removed after actuation.

The reservoir module 100 comprises a reservoir 110 that contains fluid to be injected, a piston 111, and a needle 112. The piston 111 is adapted to move in said reservoir 110 so as to inject the fluid through said needle 112. More generally, it should be understood that the term "reservoir" in the present description encompasses any type of container associated with a needle, such as a syringe or a cartridge. The needle 112 may be fastened in permanent manner to said reservoir 110 or, in a variant, the needle 112 may be put into place on the reservoir 110 before the autoinjector is actuated.

In the embodiments described in the figures, the reservoir 110 is a cartridge, preferably made of glass.

The reservoir module 100 comprises the fewest possible parts, since it is disposable, and preferably does not include a spring or any other metal part.

The reservoir module 100 includes an actuator sleeve 120 having an axial end surface that is in contact with the site that is to be injected, and includes an opening through which the needle 112 passes during the jabbing stage. After actuation, the actuator sleeve 120 covers the needle 112 of the reservoir so as to avoid any risk of pricking with said needle. The actuator sleeve 120 is adapted to slide relative to said reservoir 110 between a deployed position in which it is arranged around said needle 112, and an actuated position in which it is moved axially relative to the reservoir 110 so as to expose the needle 112.

When the reservoir 110 includes a needle 112, the reservoir module 100 includes a needle-protecting cap 130 that can be removed before using the autoinjector, advantageously by means of an appropriate removal member 135.

The driver module 200 contains the injection means and is preferably reusable. In order to be actuated, it should preferably be associated with the interface module 300, since injection is advantageously triggered by said interface module. The driver module 200 serves to cause the actuation force Fa exerted on the piston rod to vary in predetermined manner during the injection stage, as explained in greater detail below.

The driver module 200 includes a body 201 that is advantageously made up of two hollow shells that are fastened to each other. The body contains a piston rod 210 that comes into contact with the piston 111 of the reservoir 110 during actuation and moves it axially in the reservoir 110 so as to inject the fluid. The piston rod 210 is advantageously guided axially in an appropriate guide profile of the body 201, e.g. such as a rail, a groove, or a centering part through which said piston rod 210 passes.

The body 201 of the driver module 200 also contains the injection and re-cocking means that are described in greater detail below.

The interface module 300 serves to connect the driver module 200 to the reservoir module 100. It is likewise preferably reusable. The interface module 300 serves firstly to insert the reservoir module 100. When the reservoir 110 is a cartridge, as in the examples in the figures, the interface module 300 also serves to screw on the needle sub-assembly and to remove the needle-protecting cap 130. Advantageously, such screw-fastening of the needle and/or such removal of the cap is/are possible only once the reservoir module 100 has been put into place on the interface module 300. The interface module also serves both to move the actuator sleeve 120 at the beginning of actuation so as to perform jabbing and trigger the injection stage, and also to lock it in the needle safety position after injection. Finally, it also serves to remove the empty reservoir module 100 for replacing with a new reservoir module 100 that is full.

The interface module 300 comprises both a selector ring 310 that is mounted to turn relative to the driver module 200, and also pivot elements 320.

Figure 2:
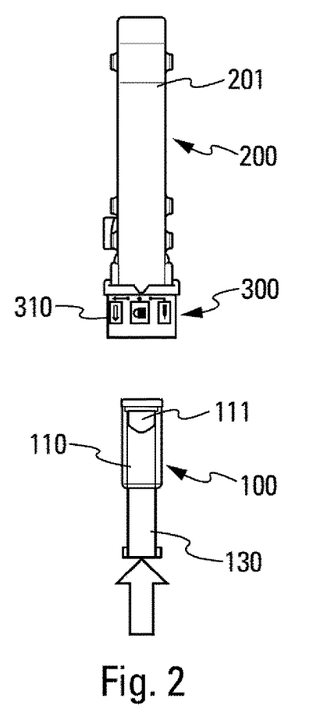
FIG. 2 is a diagrammatic side view in perspective of the FIG. 1 device as seen from another view point, shown with the interface module in place on the driver module, and before the reservoir module has been put into place.

In the position in FIG. 2, the interface module 300 is in place on the driver module 200. Before the reservoir module 100 is in place, the selector ring 310 is in its locked position in which insertion of the reservoir module 100 is possible and actuation of the driver module 200 is not possible.

Figure 3:
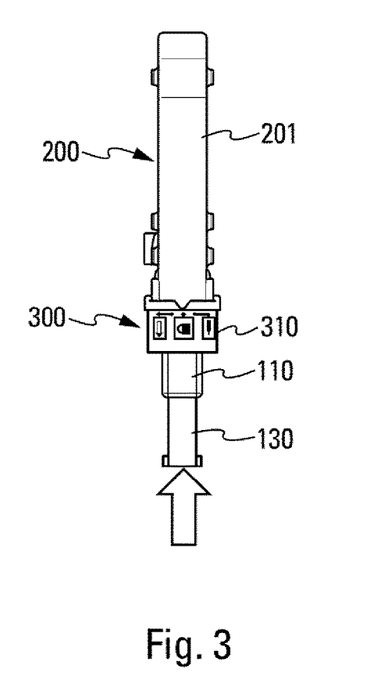
FIG. 3 is a view similar to the view in FIG. 2, shown after the reservoir module has been put into place.

The user inserts an unused reservoir module 100 into the interface module 300, as shown in FIGS. 2 and 3. Advantageously, it is not possible to insert a used reservoir module, e.g. as a result of a keying system. Optionally, a click sound can be heard when the reservoir module 100 gets into place.

Figure 4:
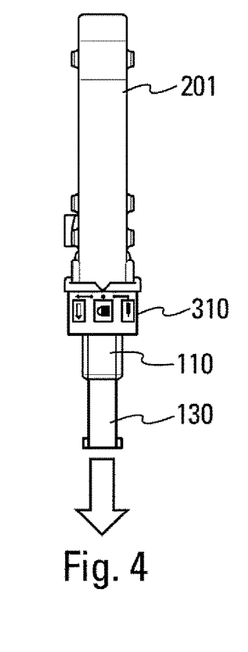
FIG. 4 is a view similar to the view in FIG. 3, shown before the needle-protecting cap has been removed.
Figure 5:
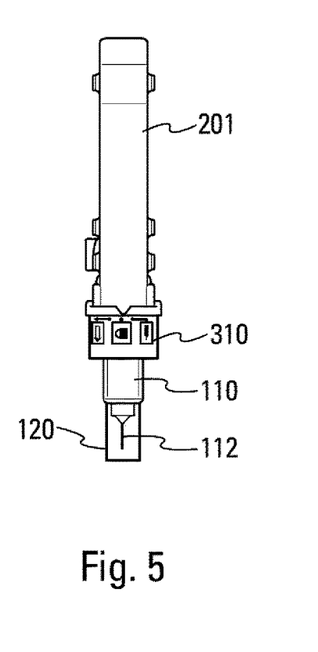
FIG. 5 is a view similar to the view in FIG. 4, shown after the needle-protecting cap has been removed.

The user then removes the needle-protecting cap 130, as shown in FIGS. 4 and 5. Optionally, when the design of the reservoir 100 does not include a needle, the needle sub-assembly is initially put into place on the reservoir module, preferably after putting said reservoir module 100 into place on the interface module 300.

Figure 6:
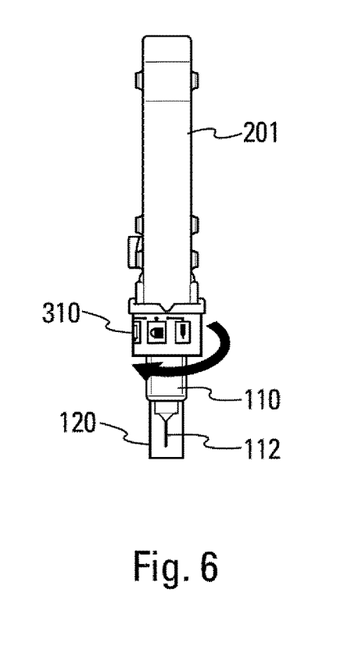
FIG. 6 is a view similar to the view in FIG. 5, shown after the interface module has been unlocked.
Figure 7:
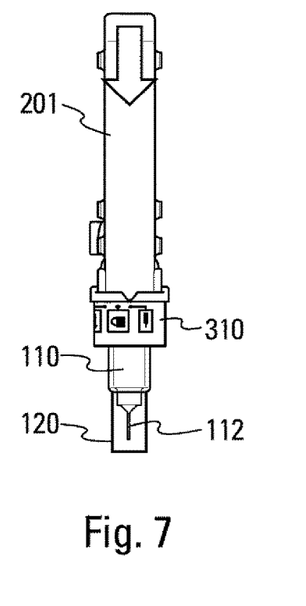
FIG. 7 is a view similar to the view in FIG. 6, shown at the beginning of actuation, before jabbing by the needle.
Figure 8:
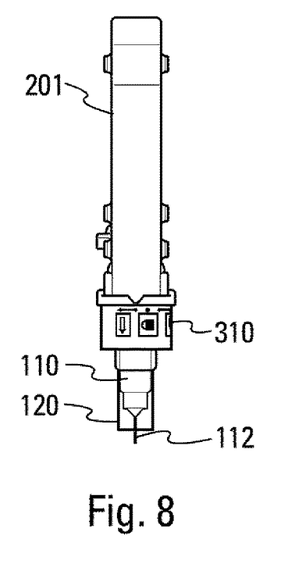
FIG. 8 is a view similar to the view in FIG. 7, shown during actuation, after jabbing by the needle, and before injection.
Figure 9:
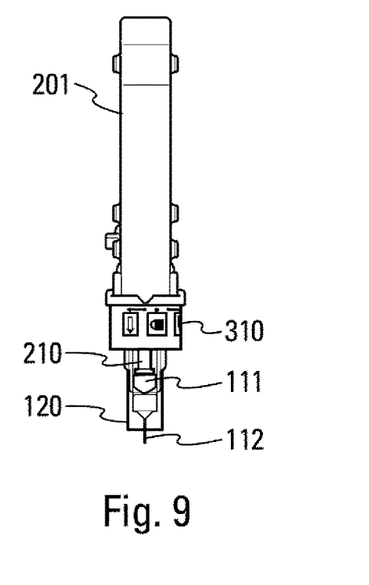
FIG. 9 is a view similar to the view in FIG. 8, shown after injection and before removal from the injection site.
Figure 10:
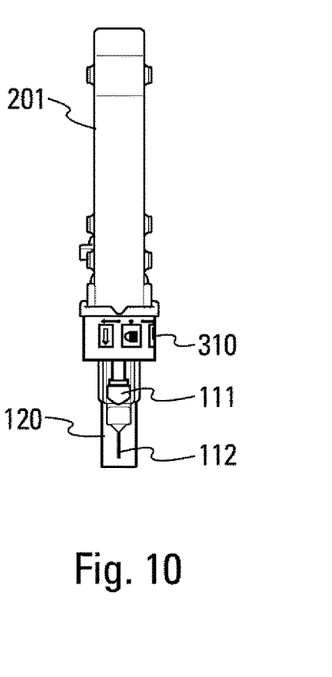
FIG. 10 is a view similar to the view in FIG. 9, shown after removal from the injection site and before the driver module has been re-cocked.
Figure 11:
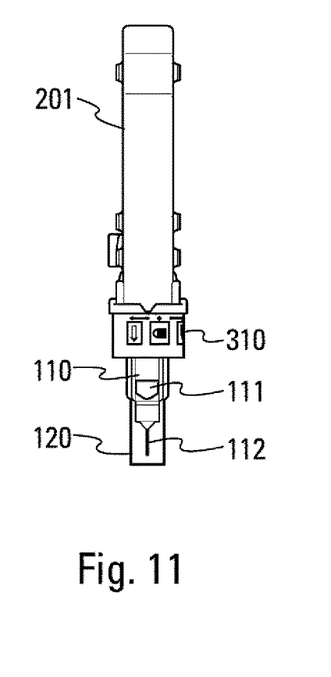
FIG. 11 is a view similar to the view in FIG. 10, shown after the driver module has been re-cocked and before the reservoir module has been unlocked.
Figure 12:
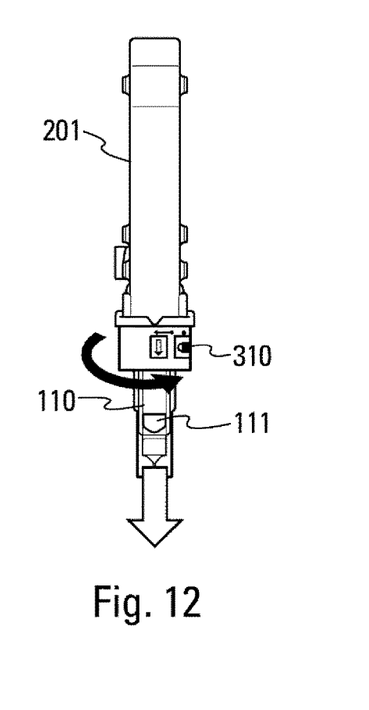
FIG. 12 is a view similar to the view in FIG. 11, shown after the reservoir module has been unlocked.

The selector ring 310 is then unlocked towards an injection position, advantageously by being turned by the user, as shown in FIG. 6.

Figure 13:
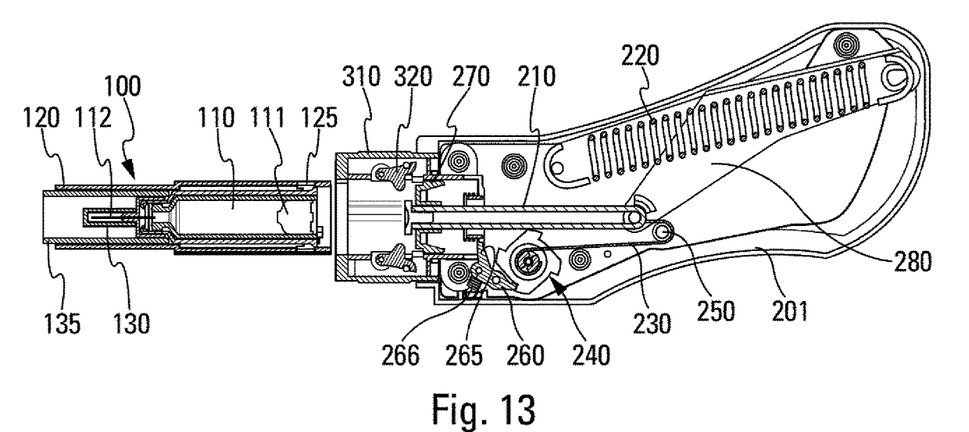
FIG. 13 is a diagrammatic section view of an autoinjector in an advantageous embodiment, shown before the reservoir module has been put into place.
Figure 14:
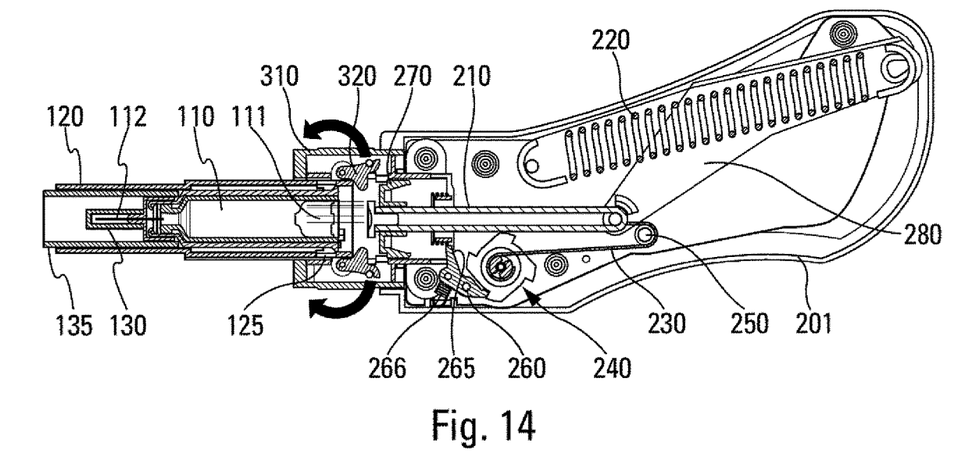
FIG. 14 is a view similar to the view in FIG. 13, shown at the beginning of the reservoir module being put into place.
Figure 15:
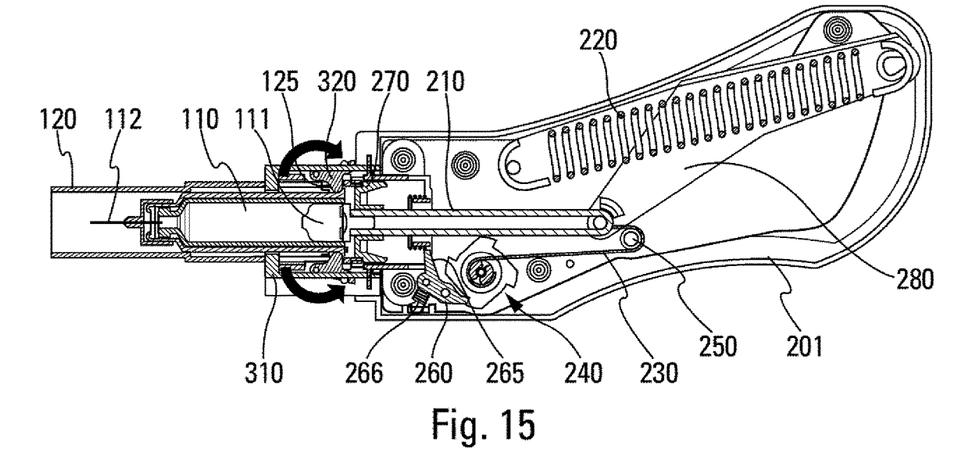
FIG. 15 is a view similar to the view in FIG. 14, shown once the reservoir module has been put into place.
Figure 16:
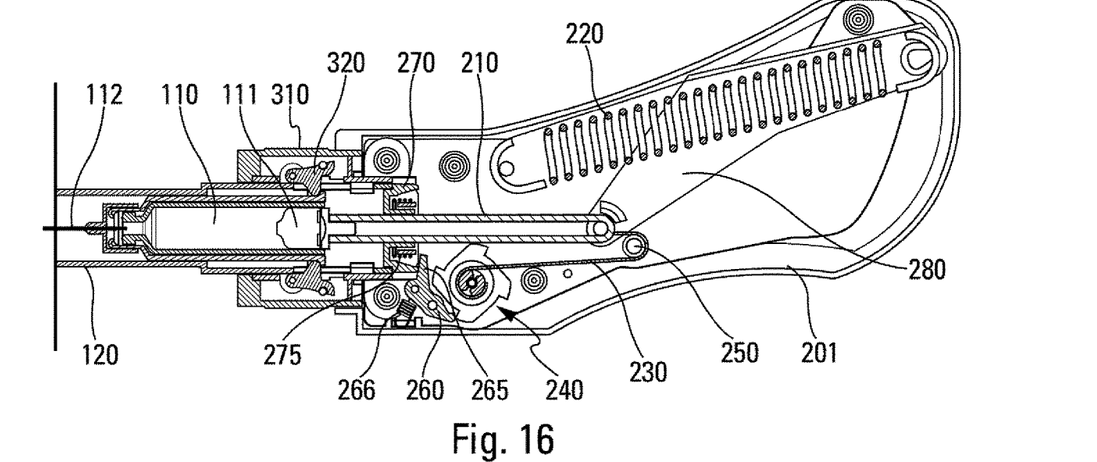
FIG. 16 is a view similar to the view in FIG. 15, shown during actuation, after jabbing by the needle, and before injection.

FIGS. 13 to 15 show the reservoir module 100 being put into place on the interface module 300. The pivot elements 320 of the interface module 300 enable the reservoir module 100 to be locked on the interface module 300.

FIGS. 7 to 10 show jabbing and injection.

At the beginning of actuation, the user presses the autoinjector against the site that is to be injected, thereby causing the actuator sleeve 120 to slide axially in the reservoir module 100, and thereby causing the needle 112 to jab into the injection site. Advantageously, the user must press with a force that is greater than a predeterminable threshold formed by a hard point that is provided so as to prevent any accidental sliding of said actuator sleeve 120.

During the jabbing stage, the selector ring 310 turns automatically towards a safety position indicating that the reservoir module 100 will be put into its needle safety position after injection during the deployment of the actuator sleeve 120.

At the end of jabbing, the actuator sleeve 120 cooperates with the lock of the driver module so as to trigger the injection stage, and the fluid contained in the reservoir 110 is expelled by the piston 111 that is thrust by the piston rod 210 being driven by force from an actuator (injection) spring 220.

When injection has ended, the user relaxes the pressure of the autoinjector against the skin and the actuator sleeve 120 deploys and becomes locked in its safety position.

The user can then re-cock the driver module 200, as described in greater detail below.

In order to eject the empty reservoir module 100, the user turns the selector ring 310 into its "ejection" position, and the reservoir 110 is unlocked and moved axially in translation through a few millimeters. The user then finishes removing the used reservoir module 100 manually.

When it is released, the selector ring 310 returns automatically into its initial locked position, and it can then no longer be moved until a new full reservoir module 100 has been put into place in the interface module 300.

Figure 17:
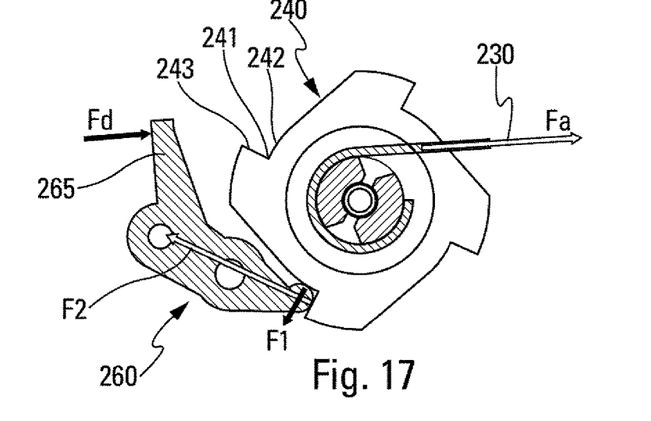
FIG. 17 is a diagrammatic section view of a detail of an injection lock in an advantageous embodiment, shown in its locked position.
Figure 18:
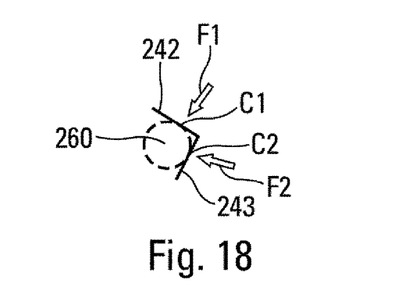
FIG. 18 is diagrammatic view of a detail of the FIG. 17 lock.
Figure 19:
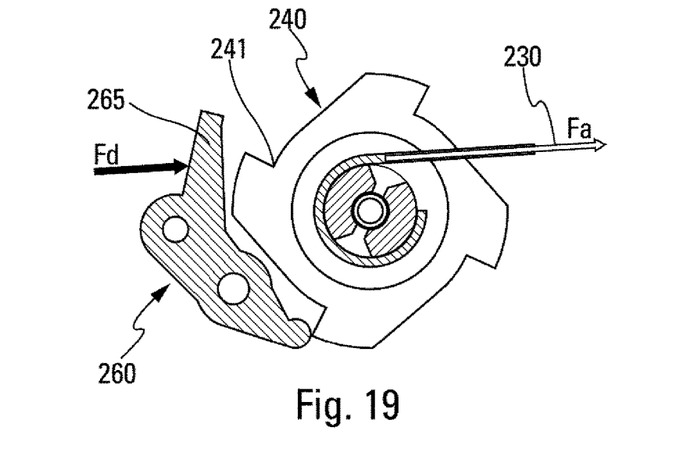
FIG. 19 is a view similar to the view in FIG. 17, shown in its unlocked position.
Figure 20:
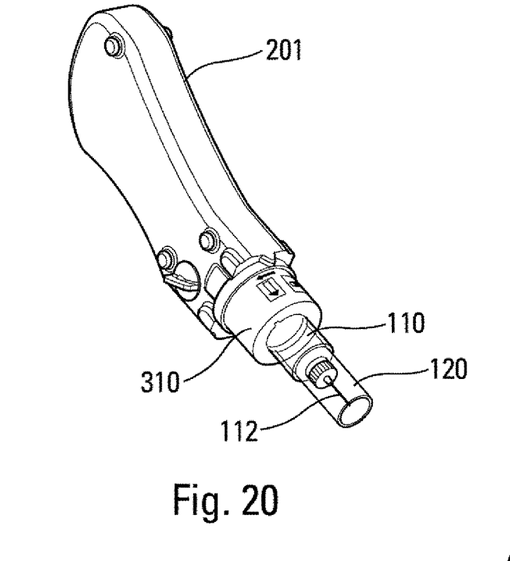
FIG. 20 is a diagrammatic side view in perspective of an autoinjector in an advantageous embodiment, shown after injection.
Figure 21:
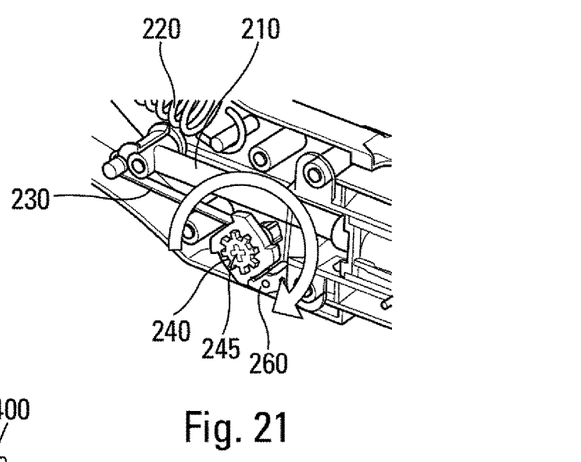
FIG. 21 is a diagrammatic and partially cut-away perspective view showing re-cocking means for re-cocking the FIG. 20 autoinjector.

FIGS. 17 to 19 show the injection lock more particularly.

In this embodiment, the piston rod 210 is connected via a belt, a wire, or thread 230 (or the like) to a toothed winder wheel 240, advantageously via a deflector wheel 250 forming a pulley. The injection spring 220 exerts an actuation force Fa on the piston rod 210, which actuation force is transmitted to the winder wheel 240 via said thread 230.

A locking member 260 co-operates with the teeth 241 of said toothed winder wheel 240, said locking member 260 being movable, in particular being pivotable, between a blocking position shown in FIG. 17, and an actuated position shown in FIG. 19.

Advantageously, a resilient element 266, e.g. a spring, urges said locking member 260 towards its blocking position.

Advantageously, in its blocking position, the locking member 260 co-operates with a tooth 241 of the winder wheel 240 with two contact points C1 and C2 that are arranged on two non-parallel surfaces 242 and 243, as can be seen in FIG. 18. This thus generates two forces F1 and F2 in different directions.

The locking member 260 includes an extension 265 that is adapted to co-operate with the actuator sleeve 120 when said actuator sleeve reaches its actuated position, i.e. once the needle 112 has jabbed into the injection site. Preferably, an intermediate ring 270 is provided between the actuator sleeve 120 and the locking member 260. Thus, after jabbing, the actuator sleeve 120 pushes against said intermediate ring 270 with an unlocking force Fd, and said intermediate ring 270 transmits the force Fd to said extension 265 of the locking member 260, thereby causing said locking member to pivot towards its actuated position. The winder wheel 240 is then no longer prevented from turning, and the injection spring 220 can move the piston rod 210 so to as to perform the injection stage.

During the injection stage, the thread 230 thus unwinds from said winder wheel 240.

During injection, the intermediate ring 270 is advantageously urged resiliently into contact with the actuator sleeve 120, e.g. by a spring 275, so that the actuator sleeve 120 is urged towards its safety position after injection.

This locking configuration serves to determine the force required from the user in order to unlock the lock and thus trigger injection. In particular, it serves to guarantee that a small force from the user unlocks a large injection force.

For example, an unlocking force Fd of 5 newtons (N) may be sufficient to unlock an injection spring 220 that is capable of exerting an actuation force Fa of about 100 N on the piston rod 210.

Furthermore, the lock forms an "engaging" system, i.e. the directions of the forces makes it possible to have a self-blocking system. Thus, an increase in the actuation force Fa strengthens the locking of the lock.

The device includes force control means for causing the force exerted by the injection spring 220 on the piston 111 of the reservoir 110 to vary in predetermined manner throughout the injection stage.

To do this, provision is made to use a lever 280 that is connected to the piston rod 210, to the injection spring 220, and to a cam 290 that is preferably secured to the body 201 of the driver module 200.

In a variant, it is possible to envisage that the cam is formed on the lever and that it co-operates with a stationary point that is secured to the body.

The injection spring 220 is advantageously fastened at one end to the body 201 and at its other end to said lever 280, which has one end that pivots on the piston rod 210 and has its other end that moves along said cam 290.

During injection, the lever 280 preferably performs both a pivoting movement about a point of the piston rod 210 and also a movement in translation relative to the body 201, these two movements being linked and performed in a single plane.

As a function of the profile of said cam 290, it is possible to determine the actuation force Fa that is applied by the injection spring 220 on the piston rod 210 throughout the injection stage.

Figure 29:
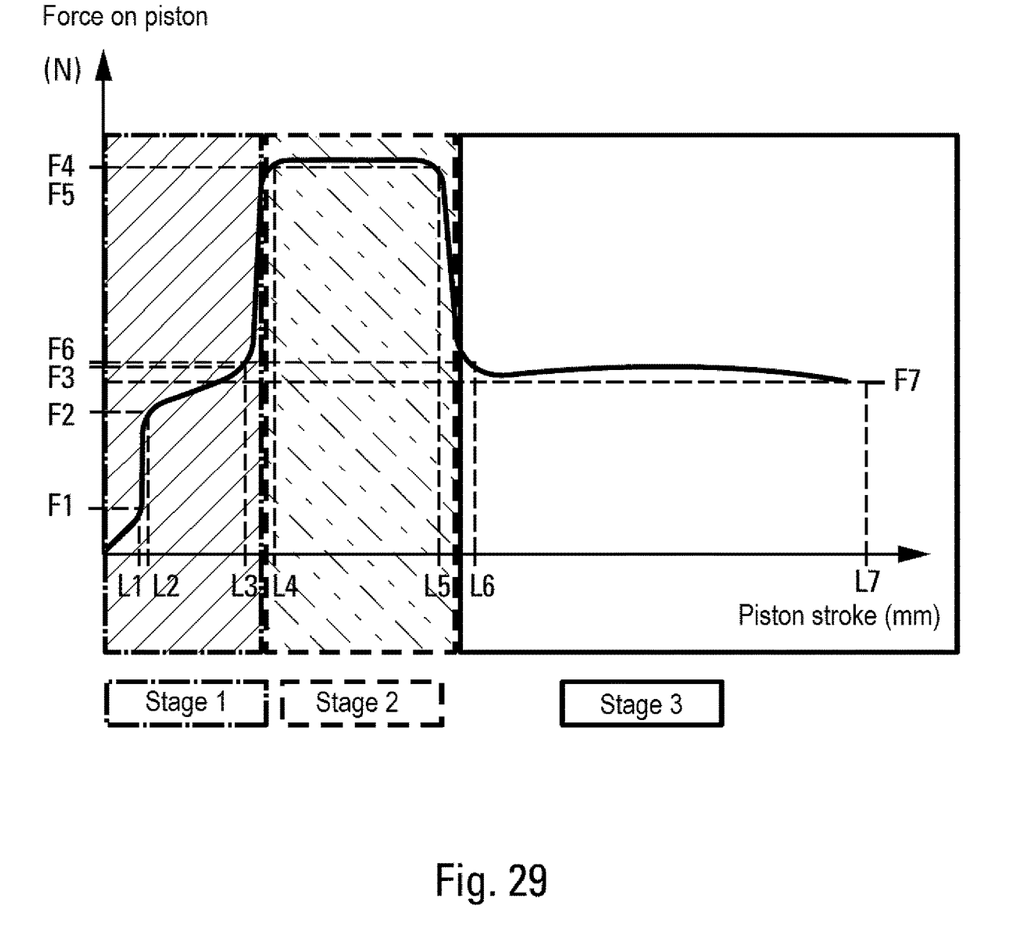
FIG. 29 plots a curve showing force during the various stages of injection, in an advantageous embodiment.

FIG. 29 is a graph plotting the force Fa in the example of the cam shown in FIGS. 25 to 28.

In this example, there are three distinct stages:
Stage 1: piston docking and compression
Stroke: 4 millimeters (mm)
Docking (section before L1):
Stroke: 2 mm
Force Fa: increasing from 0 N to 18 N
Compress stopper (section L2-L3):
Stroke: 2 mm
Force Fa: increasing from 57 N to 72 N
Stage 2: setting the fluid into motion (section L4-L5):
Stroke: 6 mm
Force Fa: constant 150 N
Stage 3: injecting the fluid (section after L6):
Stroke: 12 mm
Force Fa: constant 60 N Naturally, the numerical values are not limiting, and represent only one particular example.

Each section corresponds to a specific shape of the cam 290, and it is thus possible to predetermine any force profile by means of the cam 290.

In another variant, and by way of example, a constant actuation force Fa can be provided throughout the duration of the injection.

Advantageously, after injection, and preferably before ejection of the empty reservoir module 100, the user re-cocks the driver module 200 ready for subsequent use with another reservoir module 100.

To do this, in the example in FIGS. 13 to 22, the user rewinds the belt or the thread 230 around the winder wheel 240. This returns the piston rod 210 towards its start position, before actuation, and re-cocks the injection spring 220. The user thus turns the winder wheel 240 in the opposite direction relative to its direction in the injection stage. To do this, the winder wheel 240 includes a plurality of teeth 241 that co-operate with the locking member 260 like a non-return ratchet. When the user turns the winder wheel 240 in order to rewind the thread 230, the locking member 260 retracts and locks after each tooth 241 has passed. Thus, a higher number of teeth 241 makes it easier for the user to re-cock the driver module 200

Figure 22:
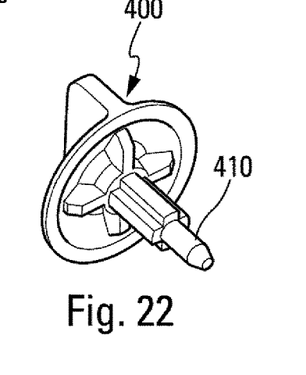
FIG. 22 is a diagrammatic perspective view of a re-cocking member that can be used with the FIG. 21 re-cocking means.

Advantageously, a re-cocking knob 400 is provided, an example of which is shown in FIG. 22. By way of example, the knob 400 may co-operate with the winder wheel 240 by means of splines 410 that match corresponding grooves 245 in the winder wheel 240. In a variant, a re-cocking shape could be formed directly on the winder wheel 240, replacing the knob. The knob 400 could also be replaced by a handle including a set of teeth that are adapted to co-operate with the winder wheel 240.

Optionally, it is possible to provide a set of cogs (not shown) so as to decrease the winding force and thus make winding easier for the user. It is then possible to provide a floating cog that co-operates firstly with the knob 400 and secondly with a set of teeth of the winder wheel 240, said floating cog being movable in an oblong hole of the body. This enables the floating cog to drive the winder wheel 240 only when it turns in one direction, without hindering the injection stage when the winder wheel 240 turns in the other direction.

Figure 23:
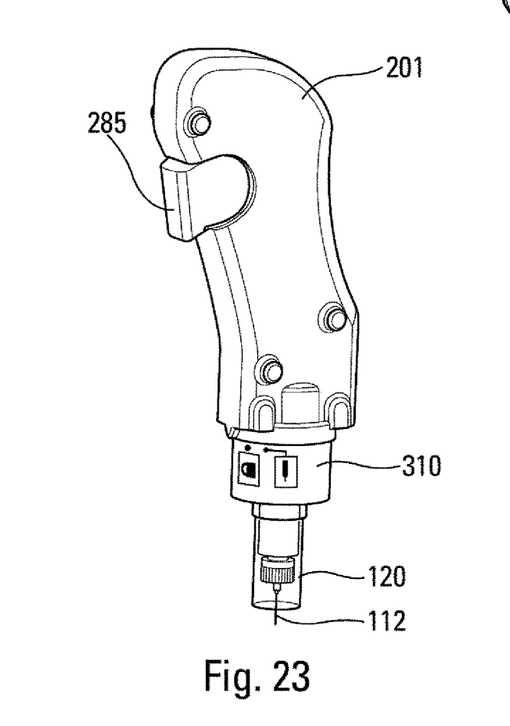
FIG. 23 is a diagrammatic side view in perspective of an autoinjector in another advantageous embodiment, shown after jabbing.
Figure 24:
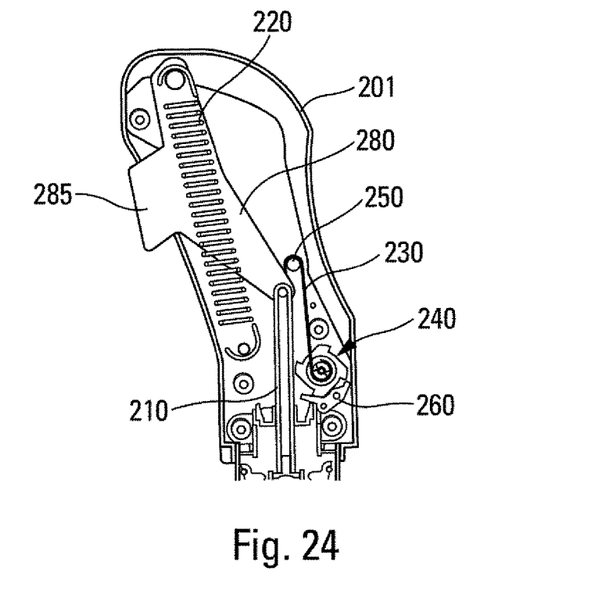
FIG. 24 is a diagrammatic and partially cut-away view of the FIG. 23 device.
Figure 25:
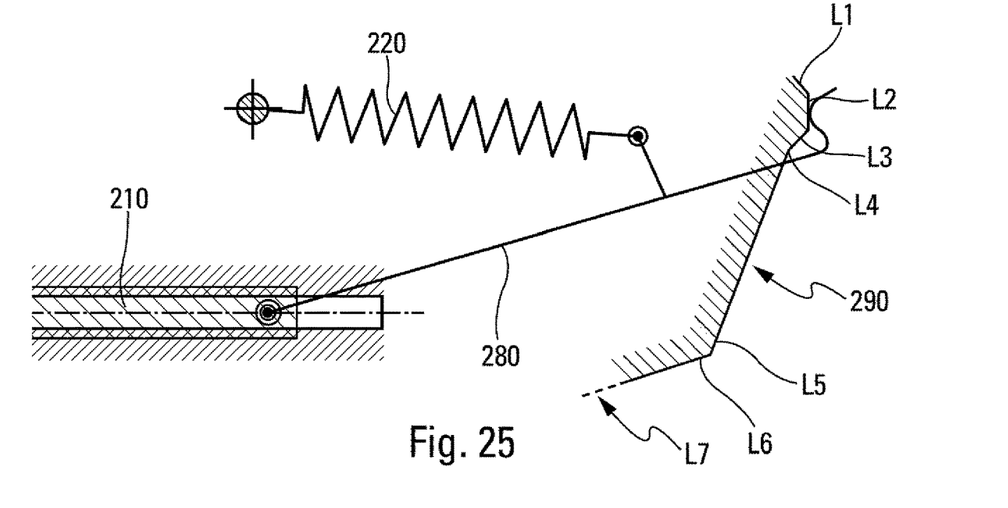
FIG. 25 is a diagram in section showing an advantageous example of a cam that makes it possible to predetermine the force profile during the injection stage.
Figure 26:
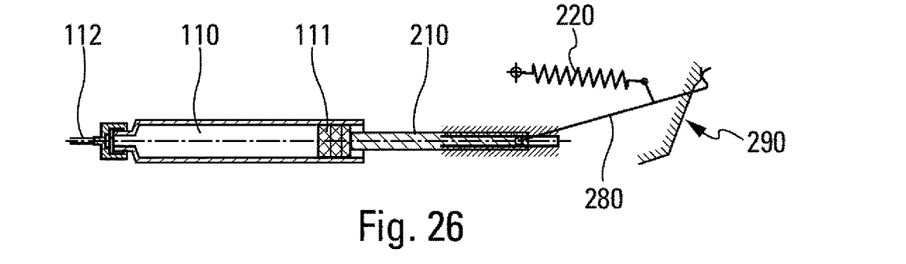
FIGS. 26 to 28 are views similar to the view in FIG. 25, showing the device successively at the beginning of injection and during injection.
Figure 27:
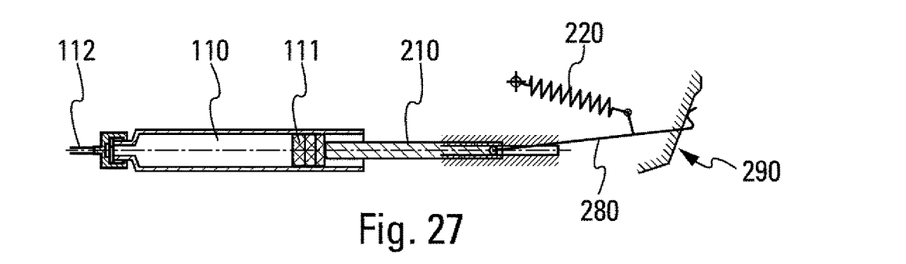
Figure 28:
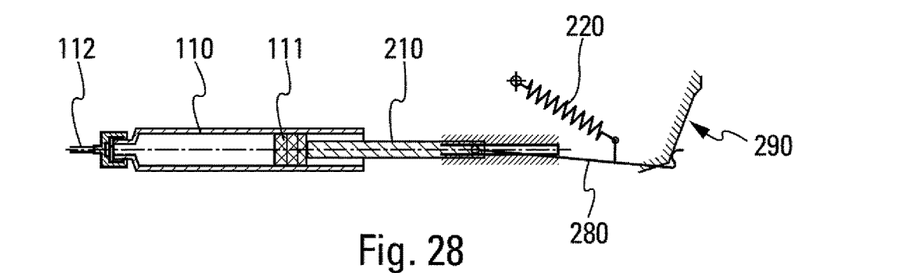

In the embodiment in FIGS. 23 and 24, provision is made to enable the user to act directly on the injection force, i.e. to manually increase the injection force. This can occur by pressing directly on the lever 280 via a portion 285 of said lever that projects out from the body 201 of the driver module 200. In a variant, it is possible to provide a connection piece that is accessible from the outside of the body 201 and that makes it possible to act on the lever 280.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to advantageous embodiments, naturally various modifications are possible for the person skilled in the art, without going beyond the ambit of the present invention, as defined by the accompanying claims.

The invention claimed is:

1. An autoinjector, comprising:
 a reservoir module comprising a reservoir containing fluid and a piston, and including a needle;
 a driver module comprising:
  a body;
  a piston rod that co-operates with the piston of said reservoir, said piston rod being moved between a rest position and an injection position in which said piston rod has moved the piston of the reservoir so as to inject the fluid through said needle;
  an injection spring for urging said piston rod towards its the injection position; and
  force control means, for causing a force exerted by said injection spring on said piston rod to vary in predetermined manner throughout the injection stage, said force control means comprising a lever and a cam, said lever being pivotally mounted at one end on said piston rod, being connected to said injection spring, and co-operating at another end with said cam; and
 an interface module that is fastened to the driver module and that receives a reservoir module before each actuation, said interface module comprising a selector ring that is mounted to turn on the driver module, and pivot elements for fastening the reservoir module in the interface module; and
 wherein said selector ring is movable in turning between a locked position in which insertion of the reservoir module is possible and actuation of the driver module is not possible, an injection position in which actuation of the driver module is possible, a safety position in which an actuator sleeve of the reservoir module returns into a deployed position around said needle, and an ejection position in which ejection of the used reservoir module is possible.

2. The autoinjector according to claim 1, wherein said reservoir module further comprises the actuator sleeve that is movable relative to said reservoir between the deployed position and an actuated position in which the actuator sleeve is moved axially relative to the reservoir as to expose the needle.

3. The autoinjector according to claim 1, wherein said injection spring is fastened at one end to said body and at another end to said lever, one end of said lever being pivotable about said piston rod and another end being movable along said cam.

4. An autoinjector, comprising:
 a reservoir module comprising a reservoir containing fluid and a piston, and including a needle;
 a driver module comprising:
  a body;
  a piston rod that co-operates with the piston of said reservoir, said piston rod being moved between a rest position and an injection position in which said piston rod has moved the piston of the reservoir so as to inject the fluid through said needle;
  an injection spring for urging said piston rod towards the injection position; and
  force control means, for causing a force exerted by said injection spring on said piston rod to vary in predetermined manner throughout the injection stage, said force control means comprising a lever and a cam, said lever being pivotally mounted at one end on said piston rod, being connected to said injection spring, and co-operating at another end with said cam; and
 an interface module that is fastened to the driver module and that receives a reservoir module before each actuation, said interface module comprising a selector ring that is mounted to turn on the driver module, and pivot elements for fastening the reservoir module in the interface module; and
 wherein said driver module includes a lock that blocks said piston rod in the rest position, said lock comprising a thread—that is connected at one end to said piston rod and at another end to a toothed winder wheel, a locking member co-operating with a tooth of said toothed winder wheel, said locking member being movable, between a blocking position which prevents the winder wheel—from turning in the direction of the actuation force (Fa) exerted by said injection spring on said piston rod, and an actuated position in which said turning of the winder wheel is possible.

5. The autoinjector according to claim 4, wherein a deflector wheel forming a pulley for the thread is provided between said piston rod and said winder wheel.

6. The autoinjector according to claim 4, wherein said locking member includes an extension that is adapted to co-operate with an actuator sleeve of the reservoir module when said needle has jabbed the site that is to be injected, so as to move said locking member towards the actuated position.

7. The autoinjector according to claim 4, including re-cocking means for rewinding said thread on said winder wheel by turning said winder wheel in a direction opposite to the direction of actuation during the injection stage.

8. The autoinjector according to claim 7, wherein the re-cocking means is a knob.

9. The autoinjector according to claim 4, wherein said locking member is pivotable.

10. The autoinjector according to claim 4, wherein said reservoir module further comprises an actuator sleeve that is movable relative to said reservoir between a deployed position in which the actuator sleeve is arranged around said needle, and an actuated position in which the actuator sleeve is moved axially relative to the reservoir as to expose the needle.

11. An autoinjector according to claim 1, An autoinjector, comprising:
- a reservoir module comprising a reservoir containing fluid and a piston, and including a needle;
- a driver module comprising:
  - a body;
  - a piston rod that co-operates with the piston of said reservoir, said piston rod being moved between a rest position and an injection position in which said piston rod has moved the piston of the reservoir so as to inject the fluid through said needle;
  - an injection spring for urging said piston rod towards the injection position; and
  - force control means, for causing a force exerted by said injection spring on said piston rod to vary in predetermined manner throughout the injection stage, said force control means comprising a lever and a cam, said lever being pivotally mounted at one end on said piston rod, being connected to said injection spring, and co-operating at another end with said cam; and
- an interface module that is fastened to the driver module and that receives a reservoir module before each actuation, said interface module comprising a selector ring that is mounted to turn on the driver module, and pivot elements for fastening the reservoir module in the interface module; and
- wherein said lever performs both a pivoting movement about a point of said piston rod and also a movement in translation relative to said body, these two movements being linked and performed in a single plane.

12. The autoinjector according to claim 11, wherein said reservoir module further comprises an actuator sleeve that is movable relative to said reservoir between a deployed position in which the actuator sleeve is arranged around said needle, and an actuated position in which the actuator sleeve is moved axially relative to the reservoir as to expose the needle.

* * * * *